(12) United States Patent
Casiraghi et al.

(10) Patent No.: US 9,394,455 B2
(45) Date of Patent: Jul. 19, 2016

(54) COPOLYMERIZABLE PHOTOINITIATORS

(71) Applicant: LAMBERTI SPA, Albizzate (IT)

(72) Inventors: Angelo Casiraghi, Milan (IT); Enzo Meneguzzo, Sesto Calende (IT); Gabriele Norcini, Comabbio (IT); Giovanni Floridi, Novara (IT); Giuseppe Li Bassi, Gavirate (IT)

(73) Assignee: IGM RESINS ITALIA S.R.L., Milan (IT)

( * ) Notice: Subject to any disclaimer, the term of this patent is extended or adjusted under 35 U.S.C. 154(b) by 0 days.

(21) Appl. No.: 14/406,453

(22) PCT Filed: Jun. 4, 2013

(86) PCT No.: PCT/EP2013/061423
§ 371 (c)(1),
(2) Date: Dec. 8, 2014

(87) PCT Pub. No.: WO2013/182533
PCT Pub. Date: Dec. 12, 2013

(65) Prior Publication Data
US 2015/0175830 A1    Jun. 25, 2015

(30) Foreign Application Priority Data

Jun. 8, 2012 (IT) .............................. VA2012A0015

(51) Int. Cl.
| | |
|---|---|
| *C07C 323/22* | (2006.01) |
| *B05D 1/00* | (2006.01) |
| *C09D 129/12* | (2006.01) |
| *C07C 49/84* | (2006.01) |
| *C08F 2/50* | (2006.01) |

(52) U.S. Cl.
CPC ................ *C09D 129/12* (2013.01); *B05D 1/00* (2013.01); *C07C 49/84* (2013.01); *C07C 323/22* (2013.01); *C08F 2/50* (2013.01)

(58) Field of Classification Search
CPC ...... C07C 45/46; C07C 49/84; C07C 323/22; C09D 129/12; C08F 2/50; B05D 1/00
See application file for complete search history.

(56) References Cited

U.S. PATENT DOCUMENTS

2006/0142408 A1    6/2006    Liu et al.
2011/0318595 A1    12/2011   Breiner et al.

FOREIGN PATENT DOCUMENTS

CA         2024862 A1    3/1991

*Primary Examiner* — Elena T Lightfoot
(74) *Attorney, Agent, or Firm* — Mossman Kumar & Tyler PC

(57) ABSTRACT

Benzophenone derivatives of formula (I) in which X is O, S or $NR_3$, and $R_3$ is H or linear or branched $C_1$-$C_{10}$ alkyl; $R_1$ is H or methyl, $R_2$ is H, halogen, linear or branched $C_1$-$C_{10}$ alkoxy, linear or branched $C_1$-$C_{10}$ alkyl, linear or branched $C_1$-$C_{10}$ alkylthio or a group $NR_4R_5$, wherein $R_4$ and $R_5$ are independently linear or branched $C_1$-$C_{10}$ alkyl, can be used as copolymerizable photoinitiators and photocrosslinkers.

(I)

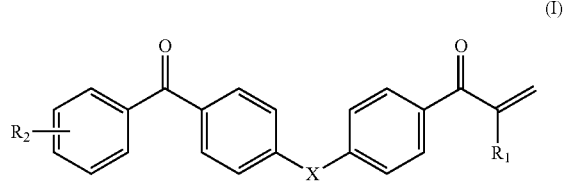

14 Claims, No Drawings

COPOLYMERIZABLE PHOTOINITIATORS

TECHNICAL FIELD

The present invention relates to copolymerizable benzophenone derivatives which can be used as copolymerizable photoinitiators with ethylenically unsaturated compounds, and to polymerizable compositions comprising the benzophenone derivatives. A method for coating a substrate by applying and photopolymerizing the polymerizable composition and a method for preparing photocrosslinked polymers is also described.

DESCRIPTION OF THE INVENTION

Photoinitiators are molecules that possess a functional group which, by exposure to light radiation of appropriate wavelength, generate radicals able to initiate polymerizations. In general, UV photo-initiators may be subdivided into Norrish type I and type II photoinitiators.

Copolymerizable photoinitiators, both of the Norrish type I and II, are a particular class of photoinitiators which participate to the polymerization reaction becoming part of the polymer chain, because of the presence in their structure of a polymerizable unsaturated group. Copolymerizable photoinitiators have the advantage of not being extracted from materials having solvent properties with which they are contacted. For this reason copolymerizable photoinitiators can be used in regulated applications, for example in coatings for food and pharmaceutical packaging.

A further application of copolymerizable photoinitiators of Norrish type II is the photocrosslinking of polymers, prepolymers and oligomers prepared through conventional chemically or thermally initiated polymerization of the copolymerizable photoinitiator and other unsaturated monomers. In this application the copolymerizable photoinitiator bound to the polymer chain, by irradiation with UV-visible light, generates radicals by extracting a hydrogen atom from a coinitiator present in the formulation or directly from the components of the polymer chain. The reaction between two radicals generates covalent bonds between the polymer chains (photocrosslinking). This application is particularly useful when it is required to change the chemical and physical characteristics of an applied coating, like the resistance to the solvents or the viscosity of the polymer, which may help to obtain adhesive properties.

CA 2024862, for example, describes the use of copolymerizable photoinitiators of Norrish type II, such as acryloyloxy benzophenone derivatives, which are used to prepare acrylic copolymers. These copolymers, thanks to their low viscosity, can be easily applied on different substrates and subsequently crosslinked to give high molecular weight polymers used as adhesives.

US 2006/0142408 describes other copolymerizable derivatives of benzophenone used in compositions based on acrylic UV-curable adhesives.

US 2011/0318595 reports the preparation of acrylic prepolymers in aqueous dispersion obtained by copolymerizing 4-methacryloyloxy benzophenone with other acrylic monomers. The polymer dispersions can be used as paints or coatings which, after UV irradiation, become particularly resistant due to the crosslinking induced by the photo-initiator present in the prepolymer.

In Journal of Applied Polymer Science: Applied Polymer Symposium 48, 533-544 (1991) the preparation of photodegradable homo- and co-polymers of unsaturated derivatives of benzophenone with styrene as comonomer is described.

The properties required to copolymerizable photoinitiators are high reactivity of their unsaturated group, in order to be consumed in the polymerization reaction, and, at the same time, high photoinitiating activity, especially at wavelength close to the visible region of the spectrum.

Now we have found high reactivity and photoinitiating activity can be obtained by substituting a benzophenone in the 4-position with a chromophore group which contains the copolymerizable unsaturated group.

These unsaturated copolymerizable benzophenone derivatives can be used as standard photoinitiators in photopolymerization reactions for various applications, such as in the coating of food and pharmaceutical packaging, or as photocrosslinking agents, if chemically or thermally copolymerized with appropriate ethylenically unsaturated compounds and further irradiated with UV-visible light, to give coatings and paints with very high resistance, adhesives by contact, etc.

DESCRIPTION OF THE INVENTION

An object of the present invention are copolymerizable benzophenones having formula I:

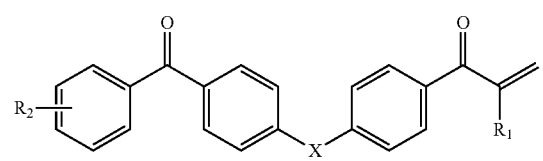

in which X is O, S or $NR_3$, and $R_3$ is H or linear or branched $C_1$-$C_{10}$ alkyl;
$R_1$ is H or methyl;
$R_2$ is H, halogen, linear or branched $C_1$-$C_{10}$ alkoxy, linear or branched $C_1$-$C_{10}$ alkyl, linear or branched $C_1$-$C_{10}$ alkylthio or a group $NR_4R_5$, wherein $R_4$ and $R_5$ are independently linear or branched $C_1$-$C_{10}$ alkyl.

It is another object of the present invention a process for preparing the copolymerizable benzophenones of formula I comprising the following steps:
A) Friedel-Crafts acylation of a diphenyl compound of formula (i),

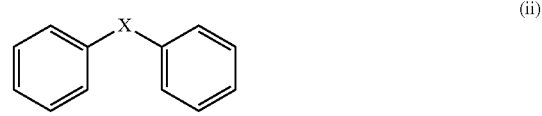

where X is S, O or $NR_3$ and $R_3$ is H or linear or branched $C_1$-$C_{10}$ alkyl, with a benzoyl halide of formula (ii),

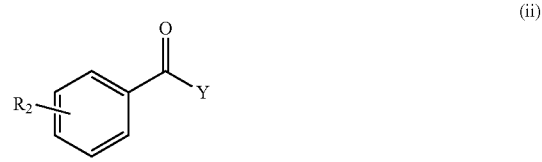

where $R_2$ is H, halogen, linear or branched $C_1$-$C_{10}$ alkoxy, linear or branched $C_1$-$C_{10}$ alkyl, linear or branched $C_1$-$C_{10}$ alkylthio or a group $NR_4R_5$, in which $R_4$ and $R_5$ are independently linear or branched $C_1$-$C_{10}$ alkyl, and Y is Cl or Br, the acylation being catalyzed by a Lewis acids and the molar ratio between the diphenyl compound of formula (i) and the benzoyl halide of formula (ii) being comprised between 1 and 1.1, to obtain an intermediate benzophenone derivative;

B) Friedel-Crafts acylation of the intermediate benzophenone derivative with an alpha-halo acyl halide of formula (iii),

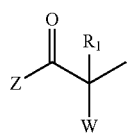

(iii)

where Z and W are independently Br or Cl and $R_1$ is H or methyl, the molar ratio of the intermediate benzophenone derivative and the alpha-halo acyl halide of formula (iii) being comprised between 1 and 1.1;

C) de-hydrohalogenation of the acylation product obtained from step B) by heating or maintaining the reaction mass at a temperature comprised between 10 and 40° C. for from 30 to 90 minutes and/or by adding further amounts of Lewis acid.

It is a further object of the present invention a polymerizable composition comprising from 80 to 99.9 parts by weight, preferably from 85 to 99 parts by weight and more preferably from 88 to 90 parts by weight, of at least one ethylenically unsaturated compound and from 0.1 to 20 parts by weight, preferably from 1 to 15 parts by weight and more preferably from 2 to 10 parts by weight, of at least one copolymerizable benzophenone of formula I.

Another aspect of the invention is directed to a method for coating a substrate comprising: a) applying on the substrate the above described polymerizable composition in such an amount to obtain, after photopolymerization, a coating with a thickness comprised between 0.2 and 100 micron; b) photopolimerizing the polymerizable composition by irradiating with a light source with emission bands in the UV-visible region.

Still another object is a method for preparing a photocrosslinked polymer comprising: a') preparing a photocrosslinkable polymer by chemically or thermally initiated radical polymerization of the above described polymerizable composition; b') applying the photocrosslinkable polymer on a substrate; c') photocrosslinking the photocrosslinkable polymer with a light source with emission bands in the UV-visible region.

DETAILED DESCRIPTION OF THE INVENTION

The preferred copolymerizable benzophenones of formula I are those in which X is O or S and $R_2$ is H, linear or branched $C_1$-$C_5$ alkyl or linear or branched $C_1$-$C_5$ alkoxy.

The most preferred copolymerizable benzophenones of formula I are those in which X is O or S, $R_1$ is methyl and $R_2$ is H.

The copolymerizable benzophenone of formula I can be prepared according to the method reported above and further detailed here below.

The Friedel Crafts acylation of step A) is performed by preparing a solution of an unsubstituted or substituted benzoyl halide of formula (ii), for example a linear or branched $C_1$-$C_{10}$ alkyl benzoyl halide, and the diphenyl compound of formula (i) in an aliphatic chlorinated solvent, such as dichloromethane, or in another suitable solvent, such as chlorobenzene, other chlorinated derivative of benzene, heptane, hexane or other aliphatic hydrocarbon having suitable volatility.

The Lewis acid, preferably $AlCl_3$, is added in portions to the so obtained solution, while maintaining the temperature between 10° C. and 30° C., preferably between 20° C. and 30° C.

Alternatively, it is also possible to prepare a solution comprising the complex formed by the acylating agent of formula (ii) and the Lewis acid and to add it dropwise to the diphenyl compound of formula (i).

The acylation reaction is exothermic and it takes from 0.5 to 10 hours, according to the efficiency of the cooling system, to be completed.

Benzoyl halides of formula (ii) are commercially available and can be used as such without any additional treatment.

The Friedel Crafts acylation of step B) is performed by adding an alpha-halo acyl-halide of formula (iii) to the reaction mixture of step A). Again the Lewis acid, preferably $AlCl_3$, is added in portions, while maintaining the temperature between 10° C. and 30° C.

The alpha-halo acyl halides of formula (iii) are liquid compounds, stable under utilization conditions, and can be easily dosed in the industrial environment. The preferred alpha-halo acyl-halide is alpha-chloro-isobutyryl chloride, corresponding to a product of formula (iii) in which Z and W are Cl.

After the dehydrohalogenation of step C), the process normally comprises decomposing the complex formed by the Lewis acid and the copolymerizable benzophenone by dropping the reaction mixture in diluted hydrochloric acid. After phase separation and washing with water, the organic phase containing the copolymerizable benzophenones of formula I is collected. Optionally the washing is performed with water containing a small amount of inorganic base, such as sodium bicarbonate or carbonate.

At the end of the process, the organic solvent can be removed by distillation. The polymerizable benzophenones of formula I may be used without further purification or may be purified by crystallization.

The solid copolymerizable benzophenones of formula I in form of powder/crystal may be obtained by crystallization of the residue obtained after distilling off the solvent from the reaction mass obtained after step C). Among the solvents useful for the crystallization are hexane, ethyl acetate and toluene, as such or in mixture with petroleum ether; isopropanol, n-propanol, ethyl alcohol or mixtures thereof, optionally in mixture with water; n-butyl alcohol; isobutyl alcohol; t-butyl alcohol.

The copolymerizable benzophenones of formula I can be mixed with ethylenically unsaturated compounds to form polymerizable compositions. With the expression "ethylenically unsaturated compounds" we mean ethylenically unsaturated monomers, oligomers, prepolymers, and mixtures thereof, that are capable of undergoing a radical polymerization.

Suitable ethylenically unsaturated compounds are (meth)acrylic esters and vinyl derivatives.

Example of (meth)acrylic esters are C1-C9 (meth)acrylic esters from linear or branched alcohols, such as methyl (meth)acrylate, ethyl (meth)acrylate, n-butyl (meth)acrylate, isobutyl (meth)acrylate, 2-ethylhexyl (meth)acrylate, propyl or isopropyl (meth)acrylate; hydroxyalkyl (meth)acrylic esters such as hydroxyethyl (meth)acrylate and hydroxypropyl (meth)acrylate; (meth)acrylic esters of unsaturated long-chain alcohols can be also used.

Vinyl derivatives from the following exemplified group may be used in the compositions of the invention: vinyl esters, vinyl ethers, vinyl halides, vinylidene halides, vinyl compounds containing aromatic rings or heterocycles in the alpha position. Specific examples are vinyl acetate, styrene, alpha-methyl styrene, viny chloride, vinyl pyridine, 1-vinyl-2-pyrrolidinone and the like.

Other suitable ethylenically unsaturated compounds are monoethylenically unsaturated mono- and/or di-carboxylic acids and/or anhydrides thereof, such as acrylic acid, methacrylic acid, fumaric acid, itaconic acid, maleic anhydride, itaconic anhydride, 4-(methacryloyloxyethyl)-trimellitic anhydride and the like. Other examples of suitable ethylenically unsaturated compounds are acrylamide and derivatives thereof, N-vinyl formamide, acrolein, methacrolein, acetoacetoxyethyl (meth)acrylate, t-octyl acrylamide, 2-(tert-butylamino) ethyl methacrylate (t-BEAM).

In a preferred embodiment the ethylenically unsaturated compounds are monomers able to undergo UV-initiated coupling reactions (H-abstraction) with the copolymerizable benzophenones of formula I.

Examples of monomers with abstractable hydrogens are (meth)acrylic ester, such as those mentioned above and in particular the branched ester, benzyl (meth)acrylate, triethanolamine (meth)acrylate, 2-(4-dimethyl amino-benzoyloxy)-ethyl (meth)acrylate.

Oligomers or prepolymers suitable as ethylenically unsaturated compounds for the present invention comprise polyesters, polyacrylates, polyurethanes, epoxy resins, polyethers with acrylic, maleic or fumaric functionalities.

The choice and relative amount of each specific ethylenically unsaturated compound making up the polymerizable compositions of the present invention depend upon the contemplated application and the desired properties and uses of the final product.

In an embodiment of the invention the polymerizable compositions can conveniently include a coinitiator, which is a molecule that acts as hydrogen donor and increases the polymerization speed. The coinitiators are known in the art and are typically alcohols, thiols, amines or ethers that have an available hydrogen which is bonded to a carbon adjacent to the heteroatom. Such coinitiators are generally present in an amount comprised between 0.2 and 15% by weight, preferably from 0.2 to 8% by weight in the polymerizable composition. Suitable coinitiators include, but are not limited to, aliphatic, cycloaliphatic, aromatic, arylaliphatic, heterocyclic, optionally oligomeric or polymeric, amines. They can be primary, secondary or tertiary amines, for example butyl amine, dibutyl amine, tributyl amine, ciclohexyl amine, benzyldimethyl amine, di-cyclohexyl amine, triethyl amine, phenyl-diethanol amine, piperidine, piperazine, morpholine, pyridine, quinoline, esters of dimethylamino benzoic acid, Michler's ketone (4,4'-bis-dimethyl aminobenzophenone). For the food packaging it is advisable to use non-extractable coinitiators, for example Esacure A198 (bis-N,N-[(4-dimethylaminobenzoyl)oxiethylen-1-yl]-methylamine).

The compositions claimed in the present invention are useful for coating substrates by photopolymerization. Preferred substrates are metallic, wood, paper or plastic surfaces. The presence of the copolymerizable benzophenones of formula I in the compositions allows the preparation of transparent, non-transparent and pigmented coatings and are useful for example also for the preparation of photopolymerizable inks.

Besides the above-mentioned ingredients, other compounds normally used in the field and known to the experts in the art can be added to the polymerizable compositions of the invention. They are, for example, thermal stabilizers, photooxidation stabilizers, anti-oxidants, fillers, dispersants, pigments, coloring and/or opacifying substances and other additives of general use. Others ingredients of the polymerizable composition of the invention can be non-photopolymerizable polymers present as chemically inert substances, such as nitrocellulose, polyacrylic esters, polyolefins etc. Preferred components are those with reactivity and toxicity characteristics suitable for the food packaging. Examples of suitable light sources for photopolymerizing the compositions of the invention are mercury or super actinic lamps; metal-halogen, i.e. iron iodide, or excimers lamps; LED with emission bands in the UV-visible region and in particular between 180 and 500 nm or laser emitting at an adequate wavelength (for example 405 nm) and with a good power. Among the suitable light sources, solar light and other sources which emit electromagnetic radiations with wavelength from 180 nm to the IR zone can be also included.

The polymerizable compositions of the present invention are particularly suitable for the preparation of coatings that are compatible with the alimentary and pharmaceutical use and in particular as components of photopolymerizable inks used for the food packaging.

The polymerizable compositions of the invention are also particularly suitable for the preparation of polymers which can be photocrosslinked in a subsequent step (photocrosslinkable polymers).

The preparation of the photocrosslinkable polymers comprising the copolymerizable benzophenones of formula I can be made by chemically or thermally initiated polymerization of the polymerizable composition, according to the conventional techniques known in the art, such as free radical techniques, in bulk, in solution, in emulsion or in dispersion using the appropriate catalysis. The polymers can be prepared by step, gradient, batch or conventional feed processes or by a continuous process. The polymers so obtained will generally have an number average molecular weight (MW) of from 20,000 to 2,000,000 g/mol, more preferably between 100,000 and 700,000 g/mol.

After preparation, the photocrosslinkable polymer is applied (spread) on the substrate and possibly the solvent is removed by evaporation.

Before application on the substrate, various additives can be added to the photocrosslinkable polymer, such as plasticizers, fillers, aging inhibitors, antioxidants, light stabilizers, ozone protectants, fatty acids, resins, nucleating agents, blowing agents, compounding agents, accelerators or it may further be of advantage to add compounds that facilitate the subsequent crosslinking. For this purpose, the photocrosslinkable polymer may optionally be blended with crosslinkers. Examples of suitable crosslinkers are ethylenically polyunsaturated compounds, such as difunctional or tri-functional acrylates, and difunctional or polyfunctional urethane acrylates.

The photocrosslinkable polymers of the invention are applied to the substrate before the photocrosslinking step, generally in an amount that generates a coating that after photocrosslinking is about 0.2 to 100 micron thick. The application may be accomplished using any conventional means, such as roller, spray, or extrusion coating. The substrate can be in the form of film, tape, sheet, panel, foam, and the like; and it can be made of materials such as paper, fabric, plastic (polyesters, PE, PP, BOPP, and PVC), nonwoven fabric, metal, glass, natural rubber, synthetic rubber, wood or plywood.

After application to the substrate, the polymer is photocrosslinked by irradiation with UV-visible light with wavelength from 180 to 500 nm. The light sources mentioned in the preceding paragraphs are suitable for the realization of the present method.

The photocrosslinked polymers according to the invention are suitable for the preparation of coatings, impregnants, adhesives and in particular of contact adhesives, which can be applied, preferably in solvent-free form, on sheet-like substrates or moldings made of metal, plastic, paper, board, leather or inorganic materials.

Examples of preparation of derivatives of copolymerizable benzophenones of formula I and of polymerizable compositions according to the invention, only for illustrative and not-limitative purpose, are described in the following paragraphs.

EXAMPLES

Example 1

Synthesis of 4-benzoyl-4'-(2-methyl-propenoyl)-diphenylether

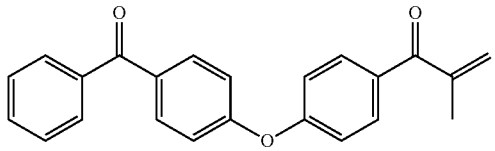 [SMILES: C=C(C)C(=O)c1ccc(Oc2ccc(C(=O)c3ccccc3)cc2)cc1]

8.24 g (0.0618 mol) of $AlCl_3$ were added in small portions in 1 hour at room temperature to a solution of 10 g (0.0588 mol) of diphenylether and 8.26 g (0.0588) of benzoyl chloride in 100 cc of $CH_2Cl_2$. After 1 hour under stirring, 8.54 g (0.0606 mol) of alpha-chloro-isobutyryl chloride were added slowly. Then 8.24 g (0.0618 mol) of $AlCl_3$ were added to the reaction mixture in small portions in 1 hour maintaining the temperature between 20 and 25° C. After the addition, the reaction mixture is stirred for 3 hours at room temperature. The mixture is then poured into 150 mL of water under vigorous stirring. The organic phase is separated, washed with water containing sodium bicarbonate in order to neutralize the acidity and bring the pH to 7-8. The solvent is distilled and the solid is crystallized from 2-propanol to give 16.36 g of product with the following characteristics:

m.p.: 108.2° C. (Gallenkamp)

1HNMR (CDCl3): δ (ppm): 2.08 (s,3H); 5.60 (s,1H); 5.88 (s,1H); 7.1 (m,4); 7.4-7.5 (m,2); 7.6 (s,1H); 7.75-7.90 (m,6).

Example 2

Synthesis of 4-benzoyl-4'-(2-methyl-propenoyl)-diphenylthioether

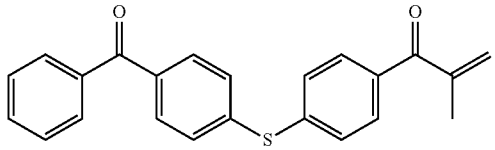 [SMILES: C=C(C)C(=O)c1ccc(Sc2ccc(C(=O)c3ccccc3)cc2)cc1]

22.40 g (0.168 mol) of $AlCl_3$ were added to a solution of 27.95 g (0.150 mol) of diphenylsulfide and 22.80 g (0.161 mol) of benzoyl chloride in 250 g of $CH_2Cl_2$ in small aliquots in 1 hour at room temperature. After 1 hour under stirring, a solution of 8.54 g (0.06057 mol) of alpha-chloroisobutyryl chloride is added slowly. The reaction mixture is cooled to 5° C. and 21.60 g (0.162 mol) of $AlCl_3$ were added in small portions in 1 hour. After the addition, the reaction mixture is poured into 300 mL of water under vigorous stirring. The organic phase was separated and washed with water containing sodium bicarbonate in order to neutralize the acidity and bring the pH to 7-8. The solvent was distilled and the so obtained 4-benzoyl-4'-(2-chloro-2-methyl-1-propanoyl)diphenylsulfide was crystallised from methanol to give 56.0 g of white solid.

28.5 g (0.214 mol) of $AlCl_3$ were added under stirring to a solution of 26.7 g (0.068 mol) of 4-benzoyl-4'-(2-chloro-2-methyl-1-propanoyl)diphenylsulfide in 220 g of $CH_2Cl_2$, in small portions in 90 minutes maintaining the temperature between 20 and 25° C. After 1 hour the reaction mixture was poured into water, the organic phase was separated, washed again with water and the solvent distilled. The residue was crystallized from 2-propanol to give 20 g of white solid.

m.p.: 107.6° C. (Gallenkamp)

1HNMR (CDCl3): δ (ppm): 2.08 (s,3H); 5.55 (s,1H); 5.95 (s,1H); 7.4-7.55 (m,6H); 7.6 (t,1H); 7.7-7.85 (m,6H).

Example 3—Comparative

Synthesis of 4-acryloyloxy-benzophenone

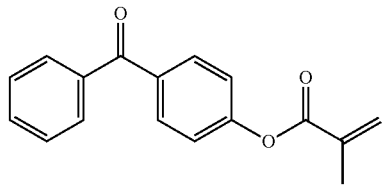 [SMILES: C=C(C)C(=O)Oc1ccc(C(=O)c2ccccc2)cc1]

1.3 g (16.25 mmoli) of NaOH 50% water solution, were added to a solution of 3 g (15.21 mmol) of 4-hydroxybenzophenone in 20 cc of methyl ethyl ketone. After 30 minutes under stirring, a solution of 1.59 g (15.21 mmol) of methacryloyl chloride in 5 mL of methyl ethyl ketone were added dropwise. After the addition the reaction mixture was stirred for 1 hour, filtered and the solvent was evaporated. The oil residue was purified by flash chromatography on silica gel (eluent $CH_2Cl_2$) to obtain 2.74 g of a colourless liquid.

¹HNMR (CDCl3): δ (ppm): 2.10 (s,3H); 5.82 (s,1H); 6.40 (s,1H); 7.2-7.3 (m,2H); 7.45-7.55 (m,2H); 7.60-7.65 (m,1H); 7.75-7.85 (m,2H); 7.85-7.95 (m,2H)

Application Tests

Evaluation of the Photoinitiating Activity.

Two clear formulations were prepared to evaluate the performance of the benzophenones of Example 2 and 3. The composition of the formulations are reported here below (% are by weight)

| | Formulation A | Formulation B* |
|---|---|---|
| Ebecryl ® 605[1] | 93.06% | 93.06% |
| Ebecryl ® 350[2] | 0.94% | 0.94% |
| Benzophenone from Ex. 2 | 3.00% | 0 |
| Benzophenone from Ex. 3 | 0 | 3.00% |
| Ethyl 4-(dimethylamino)benzoate[3] | 3.00% | 3.00% |

[1]Epoxy acrylate from Cytec
[2]Silicone diacrylate from Cytec
[3]Coinitiator
*comparative The formulations are spread on a polyethylene support as a thick film of 6 μm with a bar coater and after UV exposure (Hamamatsu Lightningcure LC8 equipped with Hg/Xe lamp 200 W and intensity reduced to 20%) the IR spectrum (Jasco FT/IR 430) is recorded.

The experiments were carried out by measuring the areas of double bond peak (1408 cm$^{-1}$) after UV irradiations at different time.

The % of polymerization was obtained according to the following formula:

$$\text{Conv \%} = [1 - (A_t/A_{t^\circ})] \times 100$$

and the results are showed in Table 1

TABLE 1

| Formulation | % after 15 sec | % after 30 sec | % after 50 sec |
|---|---|---|---|
| A | 3.26 | 20.96 | 49.7 |
| B* | 3.94 | 7.48 | 20.61 |

*Comparative

Example 4

Evaluation of the Reactivity.

To a mixture of $C_1$-$C_4$ acrylates esters (97 w/w), the copolymerizable benzophenone of Example 1 (3 w/w) is added under stirring to obtain a clear solution. The solution is poured into water (200 w/w) under stirring in the presence of surfactant and a catalyst (ammonium persulfate) and heated to 60-70° C. After 3 hours at 60-70° C. the emulsion is filtered (Emulsion C) and a sample (50 g) is hydrolyzed with NaOH 50% (50 g) under stirring at 50° C. for 3 hours, to hydrolyze and dissolve the obtained polymer. The solids are filtered off and the water is evaporated under vacuum. The solid polymer is analyzed by $^1$HNMR; the ratio between the integration of the multiplet of the aromatic hydrogens and the multiplet of the aliphatic hydrogen shows a value corresponding to 2.4%, evidencing that copolymerization actually occurred.

$^1$HNMR (D$_2$O): δ (ppm): 0.5-3.0 (m, —CH(COO$^-$)— CH$_2$—); 6.8-8.0 (m, C—H aromatic).

Example 5

Evaluation of the Photocrosslinking Activity

Test 1

A 150 micron thick layer of Emulsion C was spread on a support and dried at 70° C. for 5 minutes. The Koenig hardness (KH) of the film is measured according to standard test method ASTM 1925 after conditioning at room temperature for 1 h (KH=7 seconds) and 12 h (KH=7 seconds).

Test 2

A 150 micron thick layer of Emulsion C was spread on a support and irradiated with a Fusion Hg lamp (120 W/cm, speed 10 m/min). The Koenig hardness (KH) of the film is measured according to standard test method ASTM 1925 after conditioning at room temperature for 1 h (KH=10 seconds) and 12 h (KH=10 seconds).

The 30% increase in the KH of Test 2 evidences the photocrosslinking of the polymer induced by the presence of the benzophenone moiety and the UV light irradiation.

The invention claimed is:

1. A copolymerizable benzophenone having a general formula I:

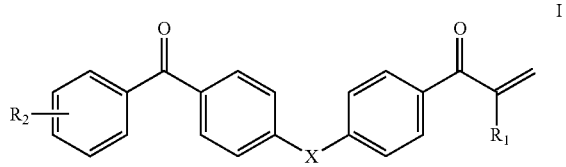

wherein:
X is O, S or NR$_3$, and R$_3$ is H or a linear or branched C$_1$-C$_{10}$ alkyl;
R$_1$ is H or methyl; and
R$_2$ is H, a halogen, a linear or branched C$_1$-C$_{10}$ alkoxy, a linear or branched C$_1$-C$_{10}$ alkyl, a linear or branched C$_1$-C$_{10}$ alkylthio or a group NR$_4$R$_5$,
wherein R$_4$ and R$_5$ are independently linear or branched C$_1$-C$_{10}$ alkyl.

2. The copolymerizable benzophenone of claim 1 wherein in formula I X is O or S and R$_2$ is H, a linear or branched C$_1$-C$_5$ alkyl or a linear or branched C$_1$-C$_5$ alkoxy.

3. The copolymerizable benzophenone of claim 2 wherein in formula I X is O or S, R$_1$ is methyl, and R$_2$ is H.

4. A process for preparing a copolymerizable benzophenone having a general formula I:

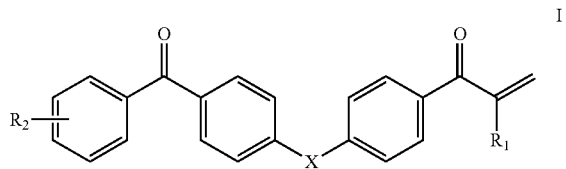

wherein:
X is O, S or NR$_3$, and R$_3$ is H or a linear or branched C$_1$-C$_{10}$ alkyl;
R$_1$ is H or methyl; and
R$_2$ is H, a halogen, a linear or branched C$_1$-C$_{10}$ alkoxy, a linear or branched C$_1$-C$_{10}$ alkyl, a linear or branched C$_1$-C$_{10}$ alkylthio or a group NR$_4$R$_5$,
wherein R$_4$ and R$_5$ are independently linear or branched C$_1$-C$_{10}$ alkyl;
comprising the steps of:
A) Friedel-Crafts acylation of a diphenyl compound of formula (i):

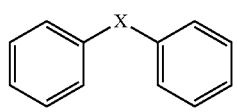

where X is S, O or NR$_3$ and R$_3$ is H or linear or branched C$_1$-C$_{10}$ alkyl, with a benzoyl halide of formula (ii),

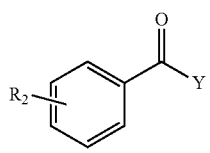

where $R_2$ is H, halogen, linear or branched $C_1$-$C_{10}$ alkoxy, linear or branched $C_1$-$C_{10}$ alkyl, linear or branched $C_1$-$C_{10}$ alkylthio or a group $NR_4R_5$, in which $R_4$ and $R_5$ are independently linear or branched $C_1$-$C_{10}$ alkyl, and Y is Cl or Br, the acylation being catalyzed by a Lewis acid and the molar ratio between the diphenyl compound of formula (i) and the benzoyl halide of formula (ii) being from about 1 to about 1.10, to obtain an intermediate benzophenone derivative;

B) Friedel-Crafts acylation of the intermediate benzophenone derivative with an alpha-halo acyl halide of formula (iii),

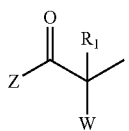

(iii)

where Z and W are independently Br or Cl and $R_1$ is H or methyl, the molar ratio of the intermediate benzophenone derivative and the alphahalo acyl halide of formula (iii) being from about 1 to about 1.1; and C) de-hydrohalogenation of the acylation product obtained from step B) by heating or maintaining the reaction mass at a temperature comprised between 10 and 40° C. for from about 30 to about 90 minutes and/or by adding further amounts of Lewis acid.

5. The process for preparing a copolymerizable benzophenone of claim 4 wherein the Lewis acid is aluminum trichloride.

6. The process for preparing a copolymerizable benzophenone of claim 4 wherein in the alpha-halo acyl halide of formula (iii), Z and W are Cl.

7. A polymerizable composition comprising from about 80 to about 99.9 parts by weight of at least one ethylenically unsaturated compound and from 0.1 to 20 parts by weight of at least one copolymerizable benzophenone of formula I

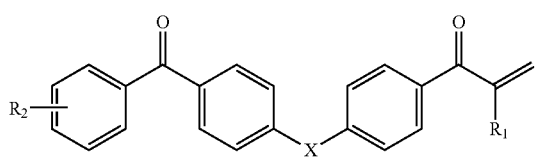

I wherein:

X is O, S or $NR_3$, and $R_3$ is H or a linear or branched $C_1$-$C_{10}$ alkyl;

$R_1$ is H or methyl; and $R_2$ is H, a halogen, a linear or branched $C_1$-$C_{10}$ alkoxy, a linear or branched $C_1$-$C_{10}$ alkyl, a linear or branched $C_1$-$C_{10}$ alkylthio or a group $NR_4R_5$, wherein $R_4$ and $R_5$ are independently linear or branched $C_1$-$C_{10}$ alkyl.

8. The polymerizable composition of claim 7 comprising from about 85 to about 99 parts by weight of at least one ethylenically unsaturated compound and from about 1 to about 15 parts by weight of the copolymerizable benzophenone of formula I.

9. The polymerizable composition of claim 7 further comprising from about 0.2 to about 15% by weight of at least one coinitiator.

10. The polymerizable composition of claim 9 wherein the coinitiator is selected from the group consisting of aliphatic, cycloaliphatic, aromatic, arylaliphatic, heterocyclic, oligomeric and polymeric amines, and combinations thereof.

11. A method for coating a substrate comprising: a) applying on the substrate a polymerizable composition of claim 7 in an amount sufficient to result in a coating, after photopolymerization, having a thickness of from about 0.2 to about 100 micron; and b) photopolymerizing the coating with a light source with emission bands in the UV-visible region.

12. The method of claim 11 wherein the polymerizable composition of claim 7, comprises from about 85 to about 99 parts by weight of at least one ethylenically unsaturated compound and from about 1 to about 15 parts by weight of the copolymerizable benzophenone of formula I.

13. The method of claim 12 further comprising from about 0.2 to about 15% by weight of at least one coinitiator.

14. The method of claim 13 wherein the coinitiator is selected from the group consisting of aliphatic, cycloaliphatic, aromatic, arylaliphatic, heterocyclic, oligomeric and polymeric amines, and combinations thereof.

* * * * *